United States Patent
Kaneko et al.

(10) Patent No.: US 9,487,689 B2
(45) Date of Patent: Nov. 8, 2016

(54) FLUORINATED COPOLYMER AND PROCESS FOR ITS PRODUCTION, WATER REPELLENT COMPOSITION, AND ARTICLE

(71) Applicant: Asahi Glass Company, Limited, Tokyo (JP)

(72) Inventors: Kyouichi Kaneko, Tokyo (JP); Kazunori Sugiyama, Tokyo (JP); Minako Shimada, Tokyo (JP); Takao Hirono, Tokyo (JP); Reika Fukuda, Tokyo (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 14/628,398

(22) Filed: Feb. 23, 2015

(65) Prior Publication Data

US 2015/0166863 A1   Jun. 18, 2015

Related U.S. Application Data

(63) Continuation of application No. PCT/JP2013/072202, filed on Aug. 20, 2013.

(30) Foreign Application Priority Data

Aug. 21, 2012 (JP) .................. 2012-182282

(51) Int. Cl.

| C09K 3/18 | (2006.01) |
|---|---|
| C08F 220/24 | (2006.01) |
| C08F 22/10 | (2006.01) |
| C08F 220/10 | (2006.01) |
| C08F 220/22 | (2006.01) |
| C07C 67/11 | (2006.01) |
| D06M 15/277 | (2006.01) |
| D06M 15/248 | (2006.01) |

(52) U.S. Cl.
CPC ................. C09K 3/18 (2013.01); C07C 67/11 (2013.01); C08F 22/10 (2013.01); C08F 220/10 (2013.01); C08F 220/22 (2013.01); C08F 220/24 (2013.01); D06M 15/248 (2013.01); D06M 15/277 (2013.01)

(58) Field of Classification Search
None
See application file for complete search history.

(56) References Cited

U.S. PATENT DOCUMENTS

| 6,653,376 B2 | 11/2003 | Sugimoto et al. | |
|---|---|---|---|
| 7,485,688 B2 | 2/2009 | Maekawa et al. | |
| 8,791,218 B2 | 7/2014 | Sugiyama et al. | |
| 8,962,751 B2 * | 2/2015 | Inoue .................... | C08F 220/22 524/755 |
| 2009/0085001 A1 | 4/2009 | Furuta et al. | |
| 2009/0325849 A1 * | 12/2009 | Gotz ..................... | C08F 214/06 510/299 |
| 2010/0331479 A1 * | 12/2010 | Sugiyama ............. | C08F 214/00 524/565 |
| 2014/0051797 A1 * | 2/2014 | Kaneko ................. | C08F 220/22 524/544 |

FOREIGN PATENT DOCUMENTS

| JP | 58-71977 | 4/1983 | |
|---|---|---|---|
| JP | 2004-269413 | 9/2004 | |
| JP | 2006-298817 | 11/2006 | |
| JP | 2009/081822 | 7/2009 | |
| JP | 2010-501656 | 1/2010 | |
| JP | WO 2011099534 A1 * | 8/2011 | ............ C08F 220/22 |
| JP | WO 2012147625 A1 * | 11/2012 | ............ C08F 220/22 |
| WO | WO 2008/143093 A1 | 11/2008 | |
| WO | WO 2009/041650 A1 | 4/2009 | |
| WO | WO 2009/148098 A1 | 12/2009 | |
| WO | WO 2010/140668 A1 | 12/2010 | |

OTHER PUBLICATIONS

U.S. Appl. No. 14/611,817, filed Feb. 2, 2015, Shimada, et al.
International Search Report issued in Application No. PCT/JP2013/072202, dated Nov. 12, 2013.

* cited by examiner

*Primary Examiner* — Nicole M Buie-Hatcher
(74) *Attorney, Agent, or Firm* — Oblon, McClelland, Maier & Neustadt, L.L.P.

(57) ABSTRACT

To provide a fluorinated copolymer comprising, in specific ratios, units derived from $F(CF_2)_6CH_2CH_2OC(O)C(CH_3)=CH_2$, units derived from vinyl chloride, units derived from vinylidene chloride, units derived from an alkyl (meth)acrylate having a $C_{12-30}$ alkyl group, and units derived from a monomer having no fluoroalkyl group and having a cross-linkable functional group, wherein units derived from $F(CF_2)_nCH_2CH_2OC(O)C(CH_3)=CH_2$ (wherein n is an integer of from 1 to 5) are in at most a specific ratio; a process for producing such a fluorinated copolymer; a water repellent composition containing such a fluorinated copolymer; and an article treated with such a water repellent composition.

17 Claims, No Drawings

FLUORINATED COPOLYMER AND PROCESS FOR ITS PRODUCTION, WATER REPELLENT COMPOSITION, AND ARTICLE

TECHNICAL FIELD

The present invention relates to a fluorinated copolymer and a process for its production, a water repellent composition, and an article.

BACKGROUND ART

As a method for imparting water repellency to the surface of an article (such as a cloth or fabric product), a method may, for example, be mentioned which comprises dipping the article in a water repellent composition made of an emulsion prepared by dispersing a fluorinated copolymer having units derived from a monomer having a fluoroalkyl group (hereinafter referred to as a "$R^f$ group") in an aqueous medium, followed by drying the article.

In recent years, EPA (US Environmental Protection Agency) has pointed out that a compound having a perfluoroalkyl group (hereinafter referred to as a "$R^F$ group") with 7 or more carbon atoms is likely to be decomposed in the environment or in vivo to accumulate decomposed products and thus tends to present high environmental burden. Therefore, a water repellent composition has been demanded which uses a fluorinated copolymer having units derived from a monomer having a $R^F$ group with at most 6 carbon atoms and having no units derived from a $R^F$ group with 7 or more carbon atoms.

As such a fluorinated copolymer, the following fluorinated copolymer has been known.

A fluorinated copolymer comprising units derived from $F(CF_2)_6CH_2CH_2OC(O)C(CH_3)=CH_2$ (hereinafter referred to as "$C_6FMA$"), units derived from $F(CF_2)_4CH_2CH_2OC(O)C(CH_3)=CH_2$, units derived from a (meth)acrylate having a $C_{12-22}$ alkyl group, at least one of units derived from vinyl chloride and units derived from vinylidene chloride, and units derived from a monomer having a cross-linkable functional group (Patent Document 1).

PRIOR ART DOCUMENT

Patent Document

Patent Document 1: JP-A-2010-501656

DISCLOSURE OF INVENTION

Technical Problem

However, in the case of the fluorinated copolymer of Patent Document 1 wherein the carbon number of the RE group is at most 6, it is particularly likely to be difficult to obtain adequate water repellency.

The present invention is to provide a fluorinated copolymer which presents little burden to the environment and is capable of imparting excellent water repellency to the surface of an article, and a process for its production, a water repellent composition using such a fluorinated copolymer, and an article having a surface treated with such a water repellent composition.

Solution to Problem

The fluorinated copolymer of the present invention is characterized by comprising from 40 to 90 mass % of units derived from the following monomer (a), from 2 to 20 mass % of units derived from the following monomer (b), from 2 to 20 mass % of units derived from the following monomer (c), from 2 to 20 mass % of units derived from the following monomer (d) and from 0.1 to 10 mass % of units derived from the following monomer (e), wherein the ratio of units derived from the following monomer (f) to the units derived from the monomer (a) is at most 10 mass ppm:

Monomer (a): $F(CF_2)_6CH_2CH_2OC(O)C(CH_3)=CH_2$,
Monomer (b): vinyl chloride,
Monomer (c): vinylidene chloride,
Monomer (d): an alkyl (meth)acrylate having a $C_{12-30}$ alkyl group,
Monomer (e): a monomer having no fluoroalkyl group and having a cross-linkable functional group,
Monomer (f): $F(CF_2)_nCH_2CH_2OC(O)C(CH_3)=CH_2$, wherein n is an integer of from 1 to 5.

In the above fluorinated copolymer, the mass ratio of the units derived from the monomer (b) to the units derived from the monomer (c) [i.e. the units derived from the monomer (b)/the units derived from the monomer (c)] is preferably from 10/90 to 90/10.

The monomer (d) is preferably an alkyl (meth)acrylate having a $C_{22-30}$ alkyl group.

The monomer (e) is preferably a (meth)acrylate having a cross-linkable functional group, an acrylamide having a cross-linkable functional group, a vinyl ether having a cross-linkable functional group, or a vinyl ester having a cross-linkable functional group.

The cross-linkable functional group of the monomer (e) is preferably a hydroxy group, a blocked isocyanate group, an N-hydroxymethylamido group or an amino group.

The monomer (e) is preferably a (meth)acrylate having a blocked isocyanate group, a (meth)acrylate having a hydroxy group, or an N-methylolacrylamide.

The fluorinated copolymer preferably further contains units derived from a monomer (g) other than the monomers (a) to (f).

The monomer (g) is preferably a cycloalkyl (meth)acrylate.

The process for producing a fluorinated copolymer of the present invention is a process comprising the following steps (I) and (II):

(I) a step of adding ethylene to $CF_3(CF_2)_5I$ obtained by a telomerization reaction of tetrafluoroethylene with at least one member selected from the group consisting of $CF_3CF_2I$ and $CF_3(CF_2)_3I$, and further reacting a methacrylic acid compound thereto to obtain a reaction solution containing the following monomer (a), followed by distillation to bring the ratio of the above monomer (f) to the above monomer (a) in the reaction solution to be at most 10 mass ppm, (II) a step of polymerizing a monomer mixture comprising from 40 to 90 mass % of the above monomer (a) obtained by the above step (I), from 2 to 20 mass % of the above monomer (b), from 2 to 20 mass % of the above monomer (c), from 2 to 20 mass % of the above monomer (d) and from 0.1 to 10 mass % of the above monomer (e) in an aqueous medium in the presence of a polymerization initiator to obtain a fluorinated copolymer.

The water repellent composition of the present invention is characterized by comprising the fluorinated copolymer of the present invention and a liquid medium.

The water repellent composition preferably contains the fluorinated copolymer emulsified in an aqueous medium.

The article of the present invention is one having a surface treated with the water repellent composition of the present invention.

Advantageous Effects of Invention

By using the fluorinated copolymer of the present invention, it is possible to obtain a water repellent composition which presents little burden on the environment and is capable of imparting excellent water repellency to the surface of an article.

According to the process for producing a fluorinated copolymer of the present invention, it is possible to produce a fluorinated copolymer which provides a water repellent composition which presents little burden on the environment and is capable of imparting excellent water repellency to the surface of an article.

The water repellent composition of the present invention presents little burden on the environment and is capable of imparting excellent water repellency to the surface of an article.

The article of the present invention presents little burden on the environment and has a surface excellent in water repellency.

DESCRIPTION OF EMBODIMENTS

In this specification, a (meth)acrylate means an acrylate or a methacrylate, and the same applies to a (meth)acrylamide, etc. Further, a monomer means a compound having a polymerizable unsaturated group. Further, a $R^f$ group is a group having some or all of hydrogen atoms in an alkyl group substituted by fluorine atoms. Further, a $R^F$ group is a group having all of hydrogen atoms in an alkyl group substituted by fluorine atoms.

In this specification, a portion derived from a monomer, which constitutes a polymer, will be referred to as a "unit derived from a monomer" or a "monomer unit".

<Fluorinated Copolymer>

The fluorinated copolymer of the present invention is a fluorinated copolymer comprising, in specific ratios, units derived from the after-mentioned monomer (a) (hereinafter referred to as "units (A)", and other units will be referred to in a similar manner), units (B) being units derived from the monomer (b), units (C) being units derived from the monomer (c), units (D) being units derived from the monomer (d), and units (E) being units derived from the monomer (e), wherein units (F) being units derived from the monomer (f) are in at most a specific ratio to the units (A).

The fluorinated copolymer of the present invention may further contain units (G) being units derived from the after-mentioned monomer (g).

[Monomer (a)]

The monomer (a) is $F(CF_2)_6CH_2CH_2OC(O)C(CH_3)=CH_2$ (C6FMA).

The fluorinated copolymer of the present invention has units (A), whereby it is capable of imparting water repellency to an article.

[Monomer (b)]

The monomer (b) is vinyl chloride.

The fluorinated copolymer of the present invention has units (B), whereby it is capable of imparting excellent water repellency to an article. Therefore, with an article surface-treated by using the fluorinated copolymer of the present invention, water will scarcely penetrate from the treated surface, and water deposited on the surface will be efficiently repelled and movable.

[Monomer (c)]

The monomer (c) is vinylidene chloride.

The fluorinated copolymer of the present invention has units (C), whereby the film-forming properties and affinity of the fluorinated copolymer to an article (such as a fabric) will be improved. Therefore, even in a case where an article is air-dried after dipped in the water repellent composition, the fluorinated copolymer tends to penetrate fully to even portions where a coating film is otherwise hardly likely to be formed by a fluorinated copolymer, like spaces among fibers in a fabric, and it is thereby possible to form a uniform and ideal coating film by the fluorinated copolymer. As a result, it is possible to impart excellent water repellency to the surface of an article and to obtain an article having the surface through which water will scarcely penetrate and on which deposited water will be efficiently repelled and movable. Further, as it has units (C), it is capable of forming a coating film excellent in washing durability.

[Monomer (d)]

The monomer (d) is an alkyl (meth)acrylate having a $C_{12-30}$ alkyl group.

The fluorinated copolymer of the present invention has units (D), whereby it is possible to improve the water repellency and at the same time to impart dynamic water repellency to the surface of an article.

The number of carbon atoms in the alkyl group in the monomer (d) is preferably from 18 to 30, more preferably from 22 to 30, from the viewpoint of the water repellency and dynamic water repellency.

The monomer (d) may, for example, be cetyl methacrylate, cetyl acrylate, stearyl methacrylate, stearyl acrylate, behenyl methacrylate or behenyl acrylate. Among them, behenyl methacrylate or behenyl acrylate is preferred from the viewpoint of the water repellency and dynamic water repellency.

[Monomer (e)]

The monomer (e) is a monomer having no $R^f$ group and having a cross-linkable functional group.

The fluorinated copolymer of the present invention has units (E), whereby it is possible to improve the water repellency and at the same time to impart dynamic water repellency to the surface of an article.

The cross-linkable functional group is preferably a functional group capable of forming at least one bond selected from the group consisting of a covalent bond, an ionic bond and a hydrogen bond, or a functional group capable of forming a cross-linking structure by an interaction of such bonds. Further, it may be a group having an active organic group or element such as hydrogen or halogen in its molecule.

As the cross-linkable functional group, a hydroxy group, an isocyanate group, a blocked isocyanate group, an alkoxysilyl group, an amino group, an N-hydroxymethylamido group, an N-alkoxymethylamido group, a silanol group, an ammonium group, an amido group, an epoxy group, an oxazoline group, a carboxy group, an alkenyl group and a sulfo group are preferred, and a hydroxy group, a blocked isocyanate group, an N-hydroxymethylamido group and an amino group are particularly preferred.

The monomer (e) is preferably a (meth)acrylate, a (meth)acrylamide, a vinyl ether or a vinyl ester.

The monomer (e) may, for example, include the following compounds.

A (meth)acrylate having a hydroxy group, such as 2-hydroxyethyl (meth)acrylate, 2-hydroxypropyl (meth)acrylate, 4-hydroxybutyl (meth)acrylate, 3-chloro-2-hydroxypropyl methacrylate or a polyoxyalkylene glycol mono(meth)acrylate.

A (meth)acrylate having an isocyanate group, such as 2-isocyanatoethyl (meth)acrylate, 3-isocyanatopropyl (meth)acrylate or 4-isocyanatobutyl (meth)acrylate.

A (meth)acrylate having a blocked isocyanate group, such as a 2-butanone oxime adduct of 2-isocyanatoethyl (meth)acrylate, a pyrazole adduct of 2-isocyanatoethyl (meth)acrylate, a 3,5-dimethylpyrazole adduct of 2-isocyanatoethyl (meth)acrylate, a 3-methylpyrazole adduct of 2-isocyanatoethyl (meth)acrylate, an ϵ-caprolactam adduct of 2-isocyanatoethyl (meth)acrylate, a 2-butanone oxime adduct of 3-isocyanatopropyl (meth)acrylate, a pyrazole adduct of 3-isocyanatopropyl (meth)acrylate, a 3,5-dimethylpyrazole adduct of 3-isocyanatopropyl (meth)acrylate, a 3-methylpyrazole adduct of 3-isocyanatopropyl (meth)acrylate, an ϵ-caprolactam adduct of 3-isocyanatopropyl (meth)acrylate, a 2-butanone oxime adduct of 4-isocyanatobutyl (meth)acrylate, a pyrazole adduct of 4-isocyanatobutyl (meth)acrylate, a 3,5-dimethylpyrazole adduct of 4-isocyanatobutyl (meth)acrylate, a 3-methylpyrazole adduct of 4-isocyanatobutyl (meth)acrylate, or an ϵ-caprolactam adduct of 4-isocyanatobutyl (meth)acrylate.

A (meth)acrylate having an alkoxysilyl group, such as 3-methacryloyloxypropyl trimethoxy silane.

A (meth)acrylate having an amino group, such as dimethylaminoethyl (meth)acrylate, diethylaminoethyl (meth)acrylate or dimethylaminopropyl (meth)acrylate.

A (meth)acrylate having an ammonium group, such as (meth)acryloyloxyethyltrimethyl ammonium chloride or (meth)acryloyloxypropyltrimethyl ammonium chloride.

A (meth)acrylate having an epoxy group, such as glycidyl (meth)acrylate.

A (meth)acrylate having a carboxy group, such as 2-(meth)acryloyloxyethyl succinic acid or 2-(meth)acryloyloxyhexahydrophthalic acid.

A (meth)acrylate having an alkenyl group, such as allyl (meth)acrylate.

A (meth)acrylamide having an amido group, such as (meth)acrylamide, N-methyl (meth)acrylamide, diacetone (meth)acrylamide or (meth)acryloylmorpholine.

An acrylamide having an N-alkoxymethylamido group, such as N-methoxymethyl (meth)acrylamide, N-ethoxymethyl (meth)acrylamide or N-butoxymethyl (meth)acrylamide.

An acrylamide having an ammonium group, such as (meth)acrylamidoethyltrimethyl ammonium chloride or (meth)acrylamidopropyltrimethyl ammonium chloride.

An acrylamide having a sulfo group, such as t-butyl (meth)acrylamide sulfonic acid.

An acrylamide having an N-hydroxymethylamido group, such as N-methylol (meth)acrylamide.

A vinyl ether having a hydroxy group, such as 2-hydroxyethyl vinyl ether, 3-hydroxypropyl vinyl ether, 2-hydroxypropyl vinyl ether, 2-hydroxyisopropyl vinyl ether, 4-hydroxybutyl vinyl ether, 4-hydroxycyclohexyl vinyl ether, hexamethylene glycol monovinyl ether, 1,4-cyclohexane dimethanol monovinyl ether, diethylene glycol monovinyl ether, triethylene glycol monovinyl ether or dipropylene glycol monovinyl ether.

A vinyl ether having an epoxy group, such as glycidyl vinyl ether.

A vinyl ether having an amino group, such as 2-aminoethyl vinyl ether, 3-aminopropyl vinyl ether or 2-aminobutyl vinyl ether.

A vinyl ether having an alkenyl group, such as allyl vinyl ether, 1,4-butane diol divinyl ether, nonane diol divinyl ether, cyclohexane diol vinyl ether, cyclohexane dimethanol divinyl ether, triethylene glycol divinyl ether, trimethylolpropane trivinyl ether or pentaerythritol tetravinyl ether.

A vinyl ester having an alkenyl group, such as a crotonic acid alkyl ester.

A vinyl ester having a carboxy group, such as a maleic acid alkyl ester, a fumaric acid alkyl ester, a citraconic acid alkyl ester, or a mesaconic acid alkyl ester.

Tri(meth)allyl isocyanurate (TAIC, TMAIC, manufactured by Nippon Kasei Chemical Co., Ltd.), triallyl cyanurate (TAC, manufactured by Nippon Kasei Chemical Co., Ltd.), phenyl glycidyl ether acrylate toluene diisocyanate urethane prepolymer (tradename "AT-600", manufactured by Kyoei Kagaku Kogyo), 3-(methyl ethyl ketoxime) isocyanate methyl-3,5,5-trimethylcyclohexyl(2-hydroxyethyl methacrylate) cyanate (tradename "Tech Coat HE-6P", manufactured by Kyoken Kasei), polycaprolactone esters of hydroxyethyl (meth)acrylate (FA and FM series of tradename "PLC", manufactured by Daicel Corporation)

(Meth)acrylic acid, 2-chloroethyl vinyl ether, trimethoxy vinyl silane, vinyl trimethoxysilane, 2-vinyl-2-oxazoline, 4-methyl-2-vinyl-2-oxazoline, 2-(meth)acryloyloxyethyl acid phosphate, etc.

From the viewpoint of the water repellency and dynamic water repellency, the monomer (e) is more preferably a (meth)acrylate having a blocked isocyanate group, a (meth)acrylate having a hydroxy group, or an acrylamide having an N-hydroxymethylamido group, most preferably a 3,5-dimethylpyrazole adduct of 2-isocyanatoethyl (meth)acrylate, a 2-butanone oxime adduct of 2-isocyanatoethyl (meth)acrylate, 2-hydroxyethyl (meth)acrylate, N-methylol (meth)acrylamide or 3-chloro-2-hydroxypropyl methacrylate.

[Monomer (f)]

The monomer (f) is $F(CF_2)_n CH_2CH_2OC(O)C(CH_3)=CH_2$, wherein n is an integer of from 1 to 5.

[Monomer (g)]

The monomer (g) is a monomer other than the monomers (a), (b), (c), (d), (e) and (f).

The monomer (g) may, for example, be isobornyl acrylate, isobornyl methacrylate, styrene, benzyl methacrylate, cyclohexyl methacrylate, tetrahydrofuryl methacrylate, phenoxyethyl methacrylate, dicyclopentanyl methacrylate, dicyclopentanyl acrylate or dicyclopentenyloxyethyl methacrylate. The monomer (g) is preferably a cycloalkyl (meth)acrylate such as isobornyl (meth)acrylate, cyclohexyl (meth)acrylate or dicyclopentanyl (meth)acrylate.

From the viewpoint of the water repellency and dynamic water repellency, the proportion of units (A) to all monomer units (100 mass %) is from 40 to 90 mass %, preferably from 60 to 80 mass %, more preferably from 65 to 75 mass %.

From the viewpoint of the water repellency and dynamic water repellency, the proportion of units (B) to all monomer units (100 mass %) is from 2 to 20 mass %, preferably from 5 to 15 mass %, more preferably from 8 to 13 mass %.

From the viewpoint of the water repellency and dynamic water repellency, the proportion of units (C) to all monomer units (100 mass %) is from 2 to 20 mass %, preferably from 5 to 15 mass %, more preferably from 8 to 13 mass %.

From the viewpoint of the water repellency and dynamic water repellency, the proportion of units (D) to all monomer units (100 mass %) is from 2 to 20 mass %, preferably from 5 to 15 mass %, more preferably from 5 to 10 mass %.

From the viewpoint of the water repellency and dynamic water repellency, the proportion of units (E) to all monomer units (100 mass %) is from 0.1 to 10 mass %, preferably from 0.5 to 5 mass %, more preferably from 1 to 3 mass %.

The proportion of units (F) to the units (A) is at most 10 mass ppm, preferably at most 6 mass ppm, more preferably at most 2 mass ppm, since excellent water repellency is thereby obtainable.

The proportion of units (G) to all monomer units (100 mass %) is preferably from 0 to 20 mass %, more preferably from 0 to 10 mass %, particularly preferably from 0 to 5 mass %.

The mass ratio (B)/(C) of units (B) to units (C) is preferably from 10/90 to 90/10, more preferably from 30/70 to 70/30, particularly preferably from 40/60 to 60/40, since excellent water repellency is thereby obtainable.

The proportions of monomer units in the fluorinated copolymer are obtained from the NMR analyses and elemental analyses. In a case where they cannot be obtained from the NMR analyses and elemental analyses, they may be calculated based on the charged amounts of monomers at the time of producing the fluorinated copolymer.

From the viewpoint of the water repellency and dynamic water repellency, the mass average molecular weight (Mw) of the fluorinated copolymer of the present invention is preferably at least 20,000, particularly preferably at least 30,000. Further, from the viewpoint of the film-forming properties and storage stability, the mass average molecular weight (Mw) of the fluorinated copolymer of the present invention is preferably at most 80,000, particularly preferably at most 60,000.

The number average molecular weight (Mn) of the fluorinated copolymer of the present invention is at least 3,000, particularly preferably at least 5,000. Further, the number average molecular weight (Mn) of the fluorinated copolymer of the present invention is at most 10,000, particularly preferably at most 8,000.

The mass average molecular weight (Mw) and the number average molecular weight (Mn) of the fluorinated copolymer are molecular weights calculated as polystyrene, as measured by gel permeation chromatography (GPC) and will be measured specifically by the following method.

The fluorinated copolymer is dissolved in tetrahydrofuran (hereinafter referred to as "THF") to obtain a 0.5 mass % solution, which is filtrated through a filter of 0.2 μm or 0.45 μm to obtain an analytical sample. With respect to such an analytical sample, the number average molecular weight (Mn) and the mass average molecular weight (Mw) are measured under the following conditions. In a case where two types of conditions are indicated in the following conditions, the condition indicated first is the condition for measurement of the sample passed through the filter of 0.2 μm, and the condition indicated secondly is the condition for measurement of the sample passed through the filter of 0.45 μm.

Measuring temperature: 23° C., 40° C.
Injected amount: 0.2 mL, 40 μL
Exit velocity: 1 mL/min., 0.35 mL/min.
Eluent: THF The fluorinated copolymer of the present invention comprises units (A) to (E) in specific ratios, wherein the content of units (F) is in a specific ratio, whereby excellent water repellency is obtainable, and on a surface-treated article, water droplets tend to be repelled and readily movable.

As a factor whereby the above effects are obtainable, it is considered to be particularly influential that the content ratio of units (F) is low. The monomer (a) is usually produced by a method which comprises adding ethylene to $CF_3(CF_2)_5I$ obtained by a telomerization reaction of tetrafluoroethylene (hereinafter referred to as "TFE") with at least one member selected from the group consisting of $CF_3CF_2I$ and $CF_3(CF_2)_3I$, and further reacting a methacrylic acid compound thereto. Further, in the above telomerization reaction, $CF_3(CF_2)_3I$ will be produced as a by-product together with the desired $CF_3(CF_2)_5I$. Further, unreacted $CF_3CF_2I$ and $CF_3(CF_2)_3I$ may remain. Therefore, in the finally obtainable reaction solution, a monomer (f) will be contained as a by-product together with the monomer (a). It is considered that in the present invention, the monomer (f) is sufficiently removed from the produced monomer (a), and the amount of units (F) contained in the fluorinated copolymer is reduced, whereby the effects by the RE groups of units (A) will be well exhibited, and excellent water repellency will be obtainable.

Further, although not necessarily clearly understood, it is considered that the monomer (b) and the monomer (c) being, when made into homopolymers, substantially different in the glass transition temperature (Tg) and their polymerization rates being different from each other, are likely to be factors whereby the excellent water repellency is obtainable. That is, the monomers (a) and (c) have higher polymerization rates than the monomer (b), and sites to exhibit excellent water repellency derived from the monomer (a) and excellent film-forming properties due to the monomer (c) with low Tg, and sites to exhibit adhesiveness and toughness derived from the monomer (b) with a low polymerization rate, are distributed in the copolymer, whereby the excellent water repellency is considered to be obtainable.

Further, the fluorinated copolymer of the present invention contains no units derived from a monomer having a RE group with 7 or more carbon atoms, whereby the contents (contents when the solid content concentration is made to be 20 mass %) of perfluorooctanoic acid (PFOA), perfluorooctane sulfonic acid (PFOS) and their precursors or analogues, of which adverse effects to the environment have been pointed out, can be made to be not higher than the detective limit as an analytical value of LC-MS/MS by the method disclosed in WO2009/081822, and environmental burdens are little.

Further, when the fluorinated copolymer of the present invention is stored as an emulsion, a decrease in pH and coloration can be prevented.

<Process for Producing Fluorinated Copolymer>

The process for producing a fluorinated copolymer of the present invention comprises the following steps (I) and (II):

(I) a step of adding ethylene to $CF_3(CF_2)_5I$ obtained by a telomerization reaction of TFE with at least one member selected from the group consisting of $CF_3CF_2I$ and $CF_3(CF_2)_3I$, and further reacting a methacrylic acid compound thereto to obtain a reaction solution containing the monomer (a), followed by distillation to bring the ratio of the monomer (f) to the monomer (a) in the reaction solution to be at most 10 mass ppm, (II) a step of polymerizing a monomer mixture comprising from 40 to 90 mass % of the monomer (a) obtained by the above step (I), from 2 to 20 mass % of the monomer (b), from 2 to 20 mass % of the monomer (c), from 2 to 20 mass % of the monomer (d) and from 0.1 to 10 mass % of the monomer (e) in an aqueous medium in the presence of a polymerization initiator to obtain a fluorinated copolymer.

[Step (I)]

For example, by the method disclosed in Japanese Patent No. 4,802,544, the telomerization reaction of TFE with at least one member selected from the group consisting of $CF_3CF_2I$ and $CF_3(CF_2)_3I$ is carried out to obtain $CF_3(CF_2)_5I$. By such a method, it is possible to highly control the chain length of the telomer to obtain $CF_3(CF_2)_5I$.

Specifically, a uniform liquid mixture wherein the molar ratio of at least one perfluoroalkyl iodide selected from the group consisting of $CF_3CF_2I$ and $CF_3(CF_2)_3I$, to TFE, is from 20/1 to 200/1, is supplied to a tubular reactor from its lower portion and moved upwards for a retention time of at least 5 minutes while maintaining the liquid state under such a condition that the reaction system would not undergo gas/liquid separation, in the presence of a radical initiator, and after letting the TFE be consumed by the telomerization reaction in the tubular reactor, $CF_3(CF_2)_5I$ is obtained from the upper portion of the reactor.

The molar ratio of the perfluoroalkyl iodide to TFE, is preferably from 10/1 to 200/1. The reaction temperature is preferably from 0 to 100° C., more preferably from 30 to 80° C.

The radical initiator may be one capable of carrying out the telomerization reaction in the liquid phase, and depending upon the reaction temperature, a common organic peroxide, azo compound or the like may be used.

Then, ethylene is reacted by addition reaction to the obtained $CF_3(CF_2)_5I$ to obtain $CF_3(CF_2)_5CH_2CH_2I$. The conditions for the addition reaction of ethylene are not particularly limited, and known conditions may be employed.

The reaction temperature is preferably from 30 to 250° C., more preferably from 50 to 220° C.

The reaction pressure is preferably at most 1 MPa, more preferably from 0.2 to 0.4 MPa.

The addition reaction of ethylene may be carried out in the presence of a catalyst which generates radicals. As the catalyst which generates radicals, an azo compound, an organic peroxide, a metal catalyst, a metal salt catalyst or the like may be mentioned.

Then, the obtained $CF_3(CF_2)_5CH_2CH_2I$ and a methacrylic acid compound are subjected to an esterification reaction to obtain the monomer (a). The conditions for the esterification reaction are not particularly limited, and known conditions may be employed.

The methacrylic acid compound may, for example, be a metal salt of methacrylic acid. The metal salt of methacrylic acid may, for example, be a salt of an alkali metal such as potassium or sodium, or a salt of an alkaline earth metal.

The reaction temperature is preferably from 160 to 220° C., more preferably from 70 to 190° C.

The solvent for the reaction may, for example, be tert-butyl alcohol.

The esterification reaction is preferably conducted in the presence of a polymerization inhibitor.

The polymerization inhibitor may, for example, be hydroquinone, p-methoxyphenol, phenothiazine, cresol, tert-butylcatechol, diphenylamine, a p-phenylenediamine or an N-oxyl compound.

In the telomerization reaction, $CF_3(CF_2)_3I$, etc. are formed as by-products in addition to the desired $CF_3(CF_2)_5I$, whereby in the reaction solution after the esterification reaction, impurities such as the monomer (f), etc. will be present in addition to the monomer (a). Therefore, purification is carried out by distillation after the esterification reaction to bring the ratio of the monomer (f) to the monomer (a) to be at most 10 mass ppm.

Specifically, it is preferred to carry out distillation by two stage distillation purification comprising the following steps.
(i-1) A step of removing a metal iodide by solid-liquid separation from the reaction solution to obtain a crude solution containing the monomer (a) and the monomer (f).
(i-2) A step of distilling the crude solution to separate it into a compound group (L) with a boiling point lower than the monomer (a) and a compound group (H) containing the monomer (a) and compounds with a boiling point higher than the monomer (a). (i-3) A step of distilling the compound group (H) to separate the monomer (a) from compounds with a boiling point higher than the monomer (a).

The monomer (f) is separated as the compound group (L) from the compound group (H) containing the monomer (a) in step (i-2).

As the method for solid-liquid separation in step (i-1), a filtration method or a centrifugal separation method is preferred. The temperature at the time of the separation is preferably from 20 to 60° C., more preferably from 30 to 40° C.

In step (i-2), the crude solution is introduced into a distillation column to separate the compound group (L) as the bottom product and the compound group (H) as the distillate. It is preferred to carry out the distillation at a temperature as low as possible to prevent a polymerization reaction from taking place.

The distillation in step (i-2) is preferably carried out under a reduced pressure. The degree of vacuum in step (i-2) is preferably from $6.67 \times 10^3$ to $66.7 \times 10^3$ Pa, more preferably from $26.7 \times 10^3$ to $40.0 \times 10^3$ Pa.

Further, in order to prevent a polymerization reaction from taking place during the distillation, it is preferred to carry out the distillation while supplying an oxygen-containing gas which contains oxygen gas.

Further, the distillation may be conducted in the presence of a polymerization inhibitor. The polymerization inhibitor may, for example, be the same one as mentioned for the esterification reaction. The amount of the polymerization inhibitor to be used, is preferably from 0.001 to 0.05 mol, more preferably from 0.01 to 0.03 mol, to 1 mol of the monomer (a).

In step (i-3), the compound group (H) is introduced into a distillation column, and the monomer (a) is taken out as a distillate. In order to prevent a polymerization reaction from taking place, it is preferred to carry out the distillation at a temperature as low as possible.

The distillation in step (i-3) is preferably carried out under a reduced pressure. The degree of vacuum in step (i-3) is preferably from $0.13 \times 10^3$ to $3.33 \times 10^3$ Pa, more preferably from $0.13 \times 10^3$ to $1.33 \times 10^3$ Pa.

Further, in order to prevent a polymerization reaction from taking place during the distillation, it is preferred to carry out the distillation while supplying an oxygen-containing gas which contains oxygen gas.

Further, the distillation may be conducted in the presence of a polymerization inhibitor. The polymerization inhibitor may, for example, be the same one as mentioned for the esterification reaction. The amount of the polymerization inhibitor to be used, is preferably from 0.001 to 0.05 mol, more preferably from 0.01 to 0.03 mol, to 1 mol of the monomer (a).

[Step (II)]

Using the distillate containing the monomer (a) after the purification in step (I), in the presence of a polymerization initiator, in an aqueous medium containing water and, as the case requires, other liquid medium, a monomer mixture comprising the monomers (a), (b), (c), (d) and (e) and, as the case requires, the monomer (g), is polymerized to form a fluorinated copolymer. In the distillate containing the monomer (a) after the purification in step (I), the content of the monomer (f) is at most 10 mass ppm to the monomer (a), and accordingly, the ratio of units (F) to units (A) in the obtainable fluorinated copolymer will be at most 10 mass ppm.

The concentrations of the monomer (a) and the monomer (f) in the distillate are measured by gas chromatographic analyses.

The polymerization method may, for example, be a dispersion polymerization, an emulsion polymerization or a suspension polymerization, and an emulsion polymerization is preferred. Further, the polymerization method may be polymerization all at once or multi-stage polymerization.

With a view to improving the yield of the fluorinated copolymer, it is preferred to preliminarily emulsify the mixture comprising the monomers and the aqueous medium before the emulsion polymerization. For example, the mixture comprising the monomers and the aqueous medium, may be mixed and dispersed by an ultrasonic stirring apparatus, a homomixer or a high pressure emulsifier.

The polymerization initiator may, for example, be a thermal polymerization initiator, a photopolymerization initiator, a radiation polymerization initiator, a radical polymerization initiator or an ionic polymerization initiator, and a water-soluble or oil-soluble radical polymerization initiator is preferred. As the radical polymerization initiator, it is possible to use a common initiator such as an azo-type polymerization initiator, a peroxide-type polymerization initiator or a Redox-type polymerization initiator depending upon the polymerization temperature. As the radical polymerization initiator, an azo-type compound is preferred, and in a case where the polymerization is carried out in an aqueous medium, a salt of an azo-type compound is more preferred.

As the azo-type compound and the salt of an azo-type compound, 2,2'-azobis(4-methoxy-2,4-dimethylvaleronitrile), 2,2'-azobis(2,4-dimethylvaleronitrile), dimethyl-2,2'-azobis(2-methylpropionate), 2,2'-azobis(2-methylbutyronitrile), 2,2'-azobis(2-methylpropionamide)dihydrochloride, 2,2'-azobis[2-(2-imidazolin-2-yl)propane]disulfide, 2,2'-azobis[2-(2-imidazolin-2-yl)propane]dihydrochloride, 2,2'-azobis[2-(2-imidazolin-2-yl)propane]acetate, 2,2'-azobis[N-(2-carboxyethyl)2-methylpropionamidine]hydrate, 2,2'-azobis(1-imino-1-pyrrolidino-2-methylpropane) dihydrochloride, etc. may be mentioned.

The amount of the polymerization initiator to be added is preferably from 0.1 to 5 parts by mass, more preferably from 0.1 to 3 parts by mass, per 100 parts by mass of the monomer mixture.

The polymerization temperature is preferably from 40 to 70° C.

At the time of polymerizing the monomer mixture, a molecular weight modifier may be used. As the molecular weight modifier, an aromatic compound, a mercapto alcohol or a mercaptan is preferred, and an alkyl mercaptan is particularly preferred.

The molecular weight modifier may, for example, be a polyfunctional mercapto compound such as mercapto ethanol, n-octyl mercaptan, n-dodecyl mercaptan, t-dodecyl mercaptan, stearyl mercaptan, thioglycerol, α-methylstyrene dimer ($CH_2$=C(Ph)$CH_2$C($CH_3$)$_2$Ph, wherein Ph is a phenyl group), diethylene glycol bis(3-mercaptobutyrate), pentaerythritol tetrakis(3-mercaptobutyrate), 2,4,6-trimercaptotriazine, or 1,3,5-tris(3-mercaptobutyloxyethyl)-1,3,5-triazine-2,4,6(1H,3H,5H)-trione.

The amount of the molecular weight modifier to be added is preferably from 0 to 5 parts by mass, more preferably from 0 to 2 parts by mass, per 100 parts by mass of the monomer mixture.

As the monomers are polymerizable substantially 100%, the proportions of the monomers (a) to (e) in the monomer mixture are the same as the proportions of the above units (A) to (E), and the same applies to the preferred embodiments.

Further, the polymerization may be carried out in the presence of a surfactant.

The solid content concentration in the emulsion immediately after the emulsion polymerization is preferably from 20 to 40 mass % in the emulsion (100 mass %). Here, the solid content concentration is a concentration including the surfactant in addition to the fluorinated copolymer. The proportion of the fluorinated copolymer in the emulsion (100 mass %) immediately after the emulsion polymerization is preferably from 18 to 40 mass %.

The solid content concentration in the emulsion is calculated from the mass of the emulsion before heating and the mass after drying it for 4 hours by a convection drying oven of 120° C.

<Water Repellent Composition>

The water repellent composition of the present invention is a composition which comprises the above-described fluorinated copolymer of the present invention and a liquid medium as essential components and may contain a surfactant and additives, as the case requires.

The water repellent composition of the present invention is preferably a composition in a liquid state, such as a solution, an emulsion or a dispersion. It is more preferably an emulsion obtained by emulsion polymerization or an emulsion obtained by diluting it with a liquid medium. In the case of diluting an emulsion obtained by emulsion polymerization, with a liquid medium, the liquid medium for dilution may be of the same type as the liquid medium in the emulsion obtained by emulsion polymerization, or may be of a type different therefrom.

The fluorinated copolymer of the present invention to be used for the water repellent composition of the present invention may be one type, or two or more types.

[Liquid Medium]

As the liquid medium, an aqueous medium or an organic solvent may be mentioned, and an aqueous medium is preferred. The aqueous medium is meant for a liquid medium composed solely of water, or a liquid medium containing at most 80 parts by mass of an organic solvent per 100 parts by mass of water.

As the organic solvent, a fluorinated organic solvent or a non-fluorinated organic solvent may be mentioned. Among them, a fluorinated organic solvent is preferred from the viewpoint of non-flammability and since it is thereby possible to form a uniform coating film with a low surface tension and little unevenness in thickness.

The fluorinated organic solvent may, for example, be dichloropentafluoropropane (tradename: AK-225, manufactured by Asahi Glass Co., Ltd.) or meta-xylene hexafluoride (mxHF, manufactured by Tokyo Chemical Industry Co., Ltd.).

The non-fluorinated organic solvent may, for example, be acetone, toluene, tetrahydrofuran or chlorobenzene.

As the organic solvent, one type may be used alone, or two or more types may be used in combination.

[Surfactant]

The surfactant may, for example, be a hydrocarbon-type surfactant and a fluorinated surfactant, and each may, for example, be an anionic surfactant, a non-ionic surfactant, a cationic surfactant or an amphoteric surfactant.

As the surfactant, from the viewpoint of the dispersion stability, a combined use of a non-ionic surfactant and a cationic surfactant or amphoteric surfactant, or a single use of an anionic surfactant, is preferred, and a combined use of a non-ionic surfactant and a cationic surfactant, is more preferred.

The content of the surfactant in the water-repellent composition (100 mass %) of the present invention is preferably from 0 to 20 mass %, more preferably from 0 to 15 mass %.

[Additives]

The additives may, for example, be a penetrating agent, a defoaming agent, a water absorbent, an antistatic agent, an antistatic polymer, a crease proofing agent, a texturing agent, a film-forming assistant, a water-soluble polymer (such as polyacrylamide or polyvinyl alcohol), a thermosetting agent (such as a melamine resin, a urethane resin, a triazine ring-containing compound or an isocyanate compound), an epoxy-curing agent (such as isophthalic acid dihydrazide, adipic acid dihydrazide, sebacic acid dihydrazide, dodecane diacid hydrazide, 1,6-hexamethylene bis(N,N-dimethyl-semicarbazide), 1,1,1',1'-tetramethyl-4,4'-(methylene-di-p-phenylene)disemicarbazide or spiro glycol), a thermosetting catalyst, a cross-linking catalyst (such as an organic acid or ammonium chloride), a synthetic resin, a fiber stabilizer, fine inorganic particles, etc.

Further, the water-repellent composition of the present invention may contain, as the case requires, a polymer capable of providing either one or both of water repellency and oil repellency (e.g. a commercially available water-repellent, a commercially available oil-repellent, a commercially available water and oil-repellent, a commercially available SR agent, etc.), a water-repellent compound having no fluorine atom, or the like.

The water-repellent compound having no fluorine atom may, for example, be a paraffin compound, an aliphatic amide compound, an alkylethylene urea compound or a silicone compound.

The solid content concentration in the water-repellent composition of the present invention at the time when it is to be used for water-repelling treatment, is preferably from 0.2 to 5 mass %, more preferably from 0.6 to 2 mass %. When the solid content concentration is at least the above lower limit value, excellent water-repellency is readily obtainable. When the solid content concentration is at most the above upper limit value, excellent water-repellency and dynamic water repellency are obtainable. The solid content concentration in the water-repellent composition of the present invention during the period after emulsion polymerization till water-repelling treatment, may be the solid content concentration in the emulsion obtained by the above emulsion polymerization, and in such a case, it may be diluted with a liquid medium and then used for the water-repelling treatment.

The solid content concentration in the water-repellent composition is calculated from the mass of the water-repellent composition before heating and the mass after drying it for 4 hours by a convection drying oven of 120° C.

The water-repellent composition of the present invention as described above contains the fluorinated copolymer of the present invention which comprises the units (A) to (E) in specific ratios, and wherein the content of the units (F) is at most a specific ratio, whereby it is possible to impart excellent water repellency to an article. Further, in the water repellent composition of the present invention, the fluorinated copolymer of the present invention contains no units derived from a monomer having a RE group with 7 or more carbon atoms, whereby the burden to the environment is little.

<Article>

The article of the present invention is one having a surface treated with the water repellent composition of the present invention.

The article to be treated may, for example, be a fabric, fibers (such as natural fibers, synthetic fibers or blended fibers), various fiber products (such as clothes), a non-woven fabric, a resin film, paper, leather, metal products, stone material, concrete products, gypsum products or glass products. The article is preferably a porous sheet-shaped article such as a fabric, a non-woven fabric, a porous resin film, paper or leather, and a fabric is particularly preferred.

The treating method may, for example, be a method of applying the water repellent composition to an article by a known coating method, followed by drying, or a method of dipping an article in the water repellent composition, followed by drying.

After treatment with the water repellent composition of the present invention, the article of the present invention may further be subjected to antistatic finish, softening finish, antibacterial finish, deodorant finish, water-proofing finish, etc.

The water-proofing finish may be a processing to impart a water-proofing film. The water-proofing film may, for example, be a porous film obtainable from a urethane resin or an acryl resin, a non-porous film obtainable from a urethane resin or an acryl resin, a polytetrafluoroethylene film, or a moisture permeable water-proofing film made of a combination thereof.

EXAMPLES

Now, the present invention will be described in detail with reference to Examples, but it should be understood that the present invention is not restricted by the following description. Ex. 1 to 12 are Production Examples, Ex. 13 to 16 are Working Examples of the present invention, and Ex. 17 to 25 are Comparative Examples.

[Evaluation Methods]
(Water Repellency (Wetting))

With respect to test cloths P and test cloths Q in Ex. 13 to 24, water repellency (wetting) was evaluated in accordance with the spray test of JIS L1092-1992. The water repellency (wetting) was represented by five grades of 1 to 5. The higher the grade, the better the water repellency (wetting).

A grade with symbol +(−) represents that as compared with the standard characteristic of that grade, the characteristic is slightly superior (inferior). Further, for example, "4-5" represents that the characteristic is intermediate between "4" and "5", and other intermediate characteristics are represented in a similar manner. The same applies to the evaluation of water repellency (repelling).

[Water Repellency (Repelling)]

With respect to test cloths P and test cloths Q in Ex. 13 to 24, rolling or flowing of water droplets was evaluated as water repellency (repelling) based on the same method as the spray test of JIS L1092-1992. The water repellency (repelling) was represented by five grades of 1 to 5. The higher the grade, the better the water repellency (repelling).

(Measurement of Advance Angle and Sweepback Angle)

On a test cloth Q4 in Ex. 13, 16, 18, 19, 21 or 22, 0.5 μL of water was dropped, and the test cloth Q4 was inclined to an inclination angle of 45°, whereby the advance angle of the water droplet (the contact angle on the lower side of the water droplet) and the sweepback angle (the contact angle on the upper side of the water droplet) were measured. The advance angle and the sweepback angle are average values of the respective angles measured with respect to five test cloths Q4. The temperature for the measurement was from 20 to 25° C.

(pH Measurement)

The pH at a temperature of 20° C. of the emulsion of the fluorinated copolymer in Ex. 4, 9, 10 or 25 was measured by a pH meter HORIBA D-54, and then, the emulsion was kept in an oven of 45° C., and upon expiration of 15 days and 30 days, the pH at a temperature of 20° C. was measured again.

(Measurement of Color Values)

The color values (L*/a*/b*) of the emulsion of the fluorinated copolymer in Ex. 4, 9, 10 or 25 were measured, and then, the emulsion was kept in an oven of 45° C., and upon expiration of 15 days and 30 days, the color values (1.*/a*/b*) were measured again. The color values (121a*/b*) were measured in accordance with JIS Z8759 by means of Chroma meter (MINOLTA CR-300), manufactured by Konica Minolta Inc.).

[Abbreviations]
(Monomer (a))
C6FMA: $F(CF_2)_6CH_2CH_2OC(O)C(CH_3)=CH_2$
(Monomer (b))
VCl: vinyl chloride
(Monomer (c))
VdCl: vinylidene chloride
(Monomer (d))
VA: behenyl acrylate
StA: stearyl acrylate
(Monomer (e))
MOI-BP: Karenz MOI-BP (registered trademark) (blocked isocyanate monomer, manufactured by Showa Denko KK)
N-MAM: N-methylol acrylamide
(Monomer (f))
CnFMA: $F(CF_2)_nCH_2CH_2OC(O)C(CH_3)=CH_2$ (wherein n is an integer of from 1 to 5)
(Monomer (g))
IB-X: isobornyl methacrylate

Ex. 1

Into a glass container, 184.2 g of C6FMA as monomer (a), 15.4 g of StA as monomer (d), 5.1 g of MOI-BP as monomer (e), 5.12 g of Emulgen 430 as a surfactant, 2.56 g of Surfynol 465 as a surfactant, 2.56 g of Pronon-204 as a surfactant, 2.56 g of Arquad 18 as a surfactant, 1.28 g of Arquad C as a surfactant, and a mixed liquid comprising 378.9 g of water and 76.8 g of dipropylene glycol, as an aqueous medium, were put, heated at 65° C. for 40 minutes and then mixed by means of a mixer (HIGH-FLEX DISPENSER HG-92, manufactured by SMT Co., LTD) to obtain a preliminary emulsion. While maintaining it at 50° C., the obtained preliminary emulsion was treated under an emulsifying pressure of 40 MPa for 1 pass by means of a high pressure emulsifier (LAB60, manufactured by Gorlin) to obtain an emulsion. C6FMA was one obtained by two-step distillation purification wherein C6FMA was separated as a bottom product and then taken out as a distillate. The ratio of CnFMA to C6FMA in the emulsion was 6 mass ppm.

The obtained emulsion was put into a stainless steel reactor and cooled to 10° C.; 25.6 g of VdCl was added as monomer (c); 1.28 g of VA-061 acetate was added as a polymerization initiator, followed by substituting the gas phase by nitrogen; VCl was injected as monomer (b); and a polymerization reaction was carried out at 60° C. for 10 hours, to obtain an emulsion of fluorinated copolymer (X-1) (solid content concentration: 35 mass %). VCl was injected in a total amount of 25.6 g.

The ratios (mass %) of the respective monomer units are shown in Table 1. The ratios of the respective units were calculated from the charged amounts during the production.

Ex. 2 to 12

Emulsions of fluorinated copolymers (X-2) to (X-4) and emulsions of fluorinated copolymers (Y-1) to (Y-8) were obtained in the same manner as in Ex. 1 except that the charged amounts of the respective monomers were changed so that the ratios (mass %) of the respective monomer units became the ratios as shown in Table 1. The charged amounts of CnFMA in Ex. 11 and 12 were adjusted by using $F(CF_2)_4CH_2CH_2OC(O)C(CH_3)=CH_2$.

TABLE 1

| | | | | | | | | | | | | | Unit: mass % | |
|---|---|---|---|---|---|---|---|---|---|---|---|---|---|---|
| | | Ex. 1 | Ex. 2 | Ex. 3 | Ex. 4 | Ex. 5 | Ex. 6 | Ex. 7 | Ex. 8 | Ex. 9 | Ex. 10 | Ex. 11 | Ex. 12 |
| Fluorinated copolymer | | X-1 | X-2 | X-3 | X-4 | Y-1 | Y-2 | Y-3 | Y-4 | Y-5 | Y-6 | Y-7 | Y-8 |
| Units (A) | C6FMA | 72 | 72 | 72 | 71 | 18 | 70 | 72 | 72 | 71 | 71 | 64.8 | 50.4 |
| Units (F) | CnFMA | | | | | | | | | | | 7.2 | 21.6 |
| Units (B) | VCl | 10 | 10 | 10 | 10 | 21 | 20 | | | | 20 | 10 | 10 |
| Units (C) | VdCl | 10 | 10 | 10 | 10 | | | 20 | 20 | 20 | | 10 | 10 |
| Units (D) | StA | 6 | 7 | | | 50.5 | 8 | 6 | 7 | | | 7 | 7 |
| | VA | | | 7 | 5 | 10 | | | | 5 | 5 | | |
| Units (G) | IB-X | | | | 3 | | | | | 3 | 3 | | |
| Units (E) | MOI-BP | 2 | | | | | 2 | 2 | | | | | |
| | N-MAM | | 1 | 1 | 1 | 0.5 | | | 1 | 1 | 1 | 1 | 1 |

Ex. 13

The emulsion of fluorinated copolymer (X-1) was diluted with water to obtain a water repellent composition having a solid content concentration of 0.6 mass %. In the obtained water repellent composition, a test cloth P formed of very fine polyester (polyethylene terephthalate) woolly and a test cloth Q formed of high density nylon taffeta were dipped and then squeezed so that the wet pickup would be 65 mass % and 57 mass %, respectively. Then, they were heated and dried at 170° C. for 60 seconds to obtain a test cloth P1 and a test cloth Q1.

Further, in the same method as described above, a test cloth P2 and a test cloth Q2 were obtained by adjusting the solid content concentration of the water repellent composition to be 1.0 mass %, a test cloth P3 and a test cloth Q3 were obtained by adjusting the solid content concentration to be 1.5 mass %, and a test cloth Q4 was obtained by adjusting the solid content concentration to be 3.0 mass %.

Ex. 14 to 24

Test cloths P1 to P3 and test cloths Q1 to Q4 were obtained in the same manner as in Ex. 13 except that the fluorinated copolymer to be used, was changed as shown in Table 2.

The evaluation results (grades) of Ex. 13 to 24 are shown in Table 2. Further, with respect to test cloths Q4 in Ex. 13, 16, 18, 19, 21 and 22, the measured results of the advance angle and the sweepback angle of a water droplet are shown in Table 3.

TABLE 2

| | | | Ex. 13 | Ex. 14 | Ex. 15 | Ex. 16 | Ex. 17 | Ex. 18 | Ex. 19 | Ex. 20 | Ex. 21 | Ex. 22 | Ex. 23 | Ex. 24 |
|---|---|---|---|---|---|---|---|---|---|---|---|---|---|---|
| Fluorinated copolymer | | | X-1 | X-2 | X-3 | X-4 | Y-1 | Y-2 | Y-3 | Y-4 | Y-5 | Y-6 | Y-7 | Y-8 |
| Water repellency (wetting) | Test cloth P (PE woolly) | P1 (0.6 mass %) | 2+ | 2 | 2+ | 2+ | 1 | 1+ | 2 | 2 | 2− | 2 | 1 | 1 |
| | | P2 (1.0 mass %) | 3+ | 3 | 3+ | 3+ | 3− | 3 | 3− | 3− | 3 | 3 | 3− | 3− |
| | | P3 (1.5 mass %) | 4+ | 4+ | 5 | 4+ | 4− | 4 | 4− | 4+ | 4 | 4+ | 4 | 4− |
| | Test cloth Q (Ny taffeta) | Q1 (0.6 mass %) | 3 | 3− | 3− | 3− | 1 | 2+ | 2 | 3− | 3− | 2+ | 2 | 2 |
| | | Q2 (1.0 mass %) | 5− | 5− | 5 | 5 | 2 | 5− | 5− | 5− | 5− | 5− | 5− | 4− |
| | | Q3 (1.5 mass %) | 5 | 5 | 5 | 5 | 3+ | 5− | 5 | 5 | 5 | 5 | 5− | 4+ |
| Water repellency (repelling) | Test cloth P (PE woolly) | P1 (0.6 mass %) | 3-4 | 3 | 3 | 3-4 | 2 | 2-3 | 3 | 3 | 3 | 3 | 2 | 2 |
| | | P2 (1.0 mass %) | 5 | 4-5 | 5 | 5 | 4 | 4-5 | 4 | 4-5 | 4-5 | 4-5 | 4 | 3-4 |
| | | P3 (1.5 mass %) | 5 | 5 | 5 | 5 | 4-5 | 4-5 | 5 | 5 | 4-5 | 4-5 | 4-5 | 4-5 |
| | Test cloth Q (Ny taffeta) | Q1 (0.6 mass %) | 3-4 | 2-3 | 3 | 3 | 1 | 3 | 2 | 2-3 | 2 | 1 | 2 | 2 |
| | | Q2 (1.0 mass %) | 4-5 | 4-5 | 4-5 | 4-5 | 2-3 | 3-4 | 4 | 4 | 4 | 4 | 4 | 3-4 |
| | | Q3 (1.5 mass %) | 5 | 5 | 5 | 5 | 3 | 3-4 | 4-5 | 4-5 | 4-5 | 4 | 4 | 4 |

TABLE 3

| | | | Ex. 13 | Ex. 16 | Ex. 18 | Ex. 19 | Ex. 21 | Ex. 22 |
|---|---|---|---|---|---|---|---|---|
| Fluorinated copolymer | | | X-1 | X-4 | Y-2 | Y-3 | Y-5 | Y-6 |
| Test cloth Q | Q4 (3.0 mass %) | Advance angle [°] | 150.7 | 151.8 | 147.9 | 147.2 | 146.6 | 146.7 |

TABLE 3-continued

| | | | Ex. 13 | Ex. 16 | Ex. 18 | Ex. 19 | Ex. 21 | Ex. 22 |
|---|---|---|---|---|---|---|---|---|
| (Ny taffeta) | mass %) | Sweep-back angle [°] | 121.7 | 121.6 | 117.9 | 121.4 | 119.8 | 117.5 |

As shown in Table 2, by the water repellent compositions in Ex. 13 to 16 of the present invention, excellent water repellency was imparted to the articles, as compared with the water repellent compositions in Ex. 17 to 22 not having either units (B) or units (C) and in Ex. 23 and 24 wherein the ratio of units (F) was high. It was confirmed that particularly, the articles treated by the water repellent compositions in Ex. 13 to 16 are excellent in the water repellency (repelling) which is regarded to be a weak point in a case where the number of carbon atoms in the RE group is at most 6.

Further, with test cloths Q4 treated by the water repellent compositions in Ex. 13 and 16 of the present invention, the advance angle and the sweepback angle were large, and the water repellency was excellent, as compared with test cloths Q4 treated by the water repellent compositions in Ex. 18, 19, 21 and 22 not having either units (B) or units (C).

Ex. 25

The emulsion of fluorinated copolymer (Y-5) obtained in Ex. 9 and the emulsion of fluorinated copolymer (Y-6) obtained in Ex. 10 were mixed at a ratio of 1:1 to obtain an emulsion containing fluorinated copolymer (Y-5) and fluorinated copolymer (Y-6) in equivalent amounts.

With respect to the emulsions of fluorinated copolymers in Ex. 4, 9, 10 and 25, changes in the pH and the color values were measured, and the results are shown in Table 4.

TABLE 4

| | | Ex. 4 X-4 | Ex. 9 Y-5 | Ex. 10 Y-6 | Ex. 25 X-5/Y-6 |
|---|---|---|---|---|---|
| pH (hydrogen ion concentration × $10^{-2}$ [mol/l] | Initial | 2.47 (0.339) | 1.87 (1.349) | 3.10 (0.078) | 2.14 (0.724) |
| | After 15 days | 2.22 (0.603) | 1.63 (2.344) | 2.55 (0.282) | 1.89 (1.288) |
| | After 30 days | 2.10 (0.794) | 1.59 (2.570) | 2.35 (0.407) | 1.82 (1.514) |
| | Difference between initial and after 30 days | 0.36 (0.437) | 0.28 (1.221) | 0.72 (0.330) | 0.32 (0.789) |
| Color values (L*/a*/b*) | Initial | 76.4/−0.7/1.3 | 67.5/5.5/19.2 | 75.6/0.5/−3.5 | 70.0/3.3/14.2 |
| | After 15 days | 73.1/0/6.6 | 62.1/8.3/19.7 | 75.3/0.4/−1.7 | 66.1/5.9/15.6 |
| | After 30 days | 74.9/0.8/8.8 | 62.1/9.0/20.6 | 76.9/0.4/−0.8 | 67.1/6.5/16.3 |

As shown in Table 4, in the emulsion of fluorinated copolymer (X-4) of the present invention in Ex. 4, an increase of the hydrogen ion concentration was prevented, and a color change to increase a reddish tint was prevented, as compared with the emulsion of fluorinated copolymer (Y-5) in Ex. 9 having units (C) without having units (B). When an increase of the hydrogen ion concentration is prevented, it is possible to prevent corrosion of an apparatus, etc. due to the water repellent composition at the time of processing of an article. Further, when a color change to increase a reddish tint is prevented, even in a case where a light-colored cloth to be processed is treated with the water repellent composition, no coloration attributable to the water repellent composition will result.

In the emulsion of fluorinated copolymer (Y-6) in Ex. 10 having units (B) without having units (C), no substantial increase of the hydrogen ion concentration and no substantial color change to increase a reddish tint are observed. Therefore, the increase of the hydrogen ion concentration and the color change to increase a reddish tint are considered to be caused by such a factor that in units (C) (vinylidene chloride units), a chlorine atom detaches together with an adjacent hydrogen atom as hydrogen chloride to form a conjugated double bond.

Further, in Ex. 25 wherein the emulsion of fluorinated copolymer (Y-5) and the emulsion of fluorinated copolymer (Y-6) were mixed, as compared with Ex. 4, no effect to prevent the increase of the hydrogen ion concentration and no effect to prevent the color change were observed. From this, it is considered that in the fluorinated copolymer of the present invention containing units (B) and units (C) at the same time, units (B) and units (C) are partly disposed to be adjacent to each other so that at such portions, chlorine atoms in units (C) (vinylidene chloride units) are prevented from detaching as hydrogen chloride, whereby the above-mentioned preventive effects are obtainable.

INDUSTRIAL APPLICABILITY

The fluorinated copolymer of the present invention is useful as a water repellent component in a water repellent composition for water repelling treatment of fabrics, fibers, various fiber products (clothes), non-woven fabrics, resin films, paper, leathers, etc.

This application is a continuation of PCT Application No. PCT/JP2013/072202, filed on Aug. 20, 2013, which is based upon and claims the benefit of priority from Japanese Patent Application No. 2012-182282 filed on Aug. 21, 2012. The contents of those applications are incorporated herein by reference in their entireties.

What is claimed is:

1. A fluorinated copolymer comprising from 40 to 90 mass % of units derived from the following monomer (a), from 2 to 20 mass % of units derived from the following monomer (b), from 2 to 20 mass % of units derived from the following monomer (c), from 2 to 20 mass % of units derived from the following monomer (d) and from 0.1 to 10 mass % of units derived from the following monomer (e), wherein the ratio of units derived from the following monomer (f) to the units derived from the monomer (a) is at most 10 mass ppm:

monomer (a): $F(CF_2)_6CH_2CH_2OC(O)C(CH_3)=CH_2$,
monomer (b): vinyl chloride,
monomer (c): vinylidene chloride,
monomer (d): an alkyl (meth)acrylate having a $C_{12-30}$ alkyl group,
monomer (e): a monomer having no fluoroalkyl group and having a cross-linkable functional group,
monomer (f): $F(CF_2)_nCH_2CH_2OC(O)C(CH_3)=CH_2$, wherein n is an integer of from 1 to 5.

2. The fluorinated copolymer according to claim 1, wherein the mass ratio of the units derived from the monomer (b) to the units derived from the monomer (c) is from 10/90 to 90/10.

3. The fluorinated copolymer according to claim 1, wherein the monomer (d) is an alkyl (meth)acrylate having a $C_{22-30}$ alkyl group.

4. The fluorinated copolymer according to claim 1, wherein the monomer (e) is a (meth)acrylate having a cross-linkable functional group, an acrylamide having a cross-linkable functional group, a vinyl ether having a cross-linkable functional group, or a vinyl ester having a cross-linkable functional group.

5. The fluorinated copolymer according to claim 1, wherein the cross-linkable functional group of the monomer (e) is a hydroxy group, a blocked isocyanate group, an N-hydroxymethylamido group or an amino group.

6. The fluorinated copolymer according to claim 1, wherein the monomer (e) is a (meth)acrylate having a blocked isocyanate group, a (meth)acrylate having a hydroxy group, or an N-methylolacrylamide.

7. The fluorinated copolymer according to claim 1, which further contains units derived from a monomer (g) other than the monomers (a) to (f).

8. The fluorinated copolymer according to claim 7, wherein the monomer (g) is a cycloalkyl (meth)acrylate.

9. A water repellent composition comprising the fluorinated copolymer as defined in claim 1 and a liquid medium.

10. The water repellent composition according to claim 9, wherein the water repellent composition contains the fluorinated copolymer emulsified in an aqueous medium.

11. An article having a surface treated with the water repellent composition as defined in claim 9.

12. The fluorinated copolymer according to claim 1, wherein monomer (d) is at least one selected from the group consisting of cetyl methacrylate, cetyl acrylate, stearyl methacrylate, stearyl acrylate, behenyl methacrylate, and behenyl acrylate.

13. The fluorinated copolymer according to claim 1, wherein monomer (d) is at least one selected from the group consisting of behenyl methacrylate and behenyl acrylate.

14. The fluorinated copolymer according to claim 1, wherein monomer (e) is at least one selected from the group consisting of a (meth)acrylate having a blocked isocyanate group, a (meth)acrylate having a hydroxy group and an acrylamide having an N-hydroxymethylamido group.

15. The fluorinated copolymer according to claim 1, wherein monomer (e) is at least one selected from the group consisting of a 3,5-dimethylpyrazole adduct of 2-isocyanatoethyl(meth)acrylate and a 2-butanoneoxime adduct of 2-isocyanatoethyl(meth)acrylate.

16. The fluorinated copolymer according to claim 1, wherein monomer (e) is at least one selected from the group consisting of 2-hydroxyethyl(meth)acrylate, N-methylol (meth)acrylamide and 3-chloromethacrylate.

17. A process for producing a fluorinated copolymer comprising the following steps (I) and (II):

(I) a step of adding ethylene to $CF_3(CF_2)_5I$ obtained by a telomerization reaction of tetrafluoroethylene with at least one member selected from the group consisting of $CF_3CF_2I$ and $CF_3(CF_2)_3I$, and further reacting a methacrylic acid compound thereto to obtain a reaction solution containing the following monomer (a), followed by distillation to bring the ratio of the following monomer (f) to the monomer (a) in the reaction solution to be at most 10 mass ppm, (II) a step of polymerizing a monomer mixture comprising from 40 to 90 mass % of the monomer (a) obtained by the above step (I), from 2 to 20 mass % of the following monomer (b), from 2 to 20 mass % of the following monomer (c), from 2 to 20 mass % of the following monomer (d) and from 0.1 to 10 mass % of the following monomer (e) in an aqueous medium in the presence of a polymerization initiator to obtain a fluorinated copolymer:

monomer (a): $F(CF_2)_6CH_2CH_2OC(O)C(CH_3)=CH_2$,
monomer (b): vinyl chloride,
monomer (c): vinylidene chloride,
monomer (d): an alkyl (meth)acrylate having a $C_{12-30}$ alkyl group,
monomer (e): a monomer having no fluoroalkyl group and having a cross-linkable functional group,
monomer (f): $F(CF_2)_nCH_2CH_2OC(O)C(CH_3)=CH_2$ wherein n is an integer of from 1 to 5.

* * * * *